United States Patent [19]

Akimova et al.

[11] Patent Number: 4,847,065
[45] Date of Patent: Jul. 11, 1989

[54] COMPOSITION FOR OCCLUSION OF DUCTS AND CAVITIES OF HUMAN BODY

[76] Inventors: Alla Y. Akimova, ulitsa Petrozavodskaya,5, korpus 3, kv. 391; Valentin M. Buyanov, Komsomolsky prospekt, 36, kv. 48; Eduard I. Galperin, ulitsa Konjushkovskaya, 30, kv. 28; Anatoly B. Davydov, ulitsa Krasny Kazanets, 19, korpus 1, kv. 283; Valery N. Egiev, Volgogradsky prospekt, 71 korpus 1, kv. 156; Svetlana M. Kremli, 5 Voikovsky proezd,10,kv. 63; Nikolai F. Kuzovlev, ulitsa Erevanskaya, 15, korpus 1, kv. 19; Natalya A. Lukyanova, ulitsa Rybinskaya, 21, korpus 2, kv. 118; Valeria I. Timokhina, Yaroslavskoe shosse, 4, korpus 4, kv. 373, all of Moscow, U.S.S.R.

[21] Appl. No.: 10,904

[22] Filed: Feb. 4, 1987

[51] Int. Cl.$^4$ ............................................. A61K 49/04
[52] U.S. Cl. ..................................................... 424/5
[58] Field of Search ............................................ 424/5

[56] References Cited

U.S. PATENT DOCUMENTS 4,359,454 11/1982 Hoffman ................................. 424/5
4,407,793 10/1983 Akimova et al. .................... 424/154
4,713,235 12/1987 Krall ...................................... 424/5

OTHER PUBLICATIONS

D. F. Blagovidov et al., in the journal 'Klinicheskaya Khirurugia' 1982, No. 11, pp. 10–14.
Gebhardt Ch., Stolte M. Lang. Arch. Chir., 1978, Bd. 346, H.3, S. 149–166.
Little, J. M., Laner C. Gurgery, 1977, vol. 81, No. 3, pp. 243–249.

Primary Examiner—Frederick E. Waddell
Attorney, Agent, or Firm—Ladas & Parry

[57] ABSTRACT

The present invention relates to compositions for occlusion of ducts and cavities of human body.

The composition incorporates alpha-cyanoacrylates, dimethylsulphoxide, dimethylketone and an iodine-containing radiopaque organic acid, or mixtures of such acids, the weight percentage ratio of the original constituents being as follows:
- alpha-cyanoacrylate: 25 to 42
- dimethylsulphoxide: 12 to 25
- dimethylketone: 20 to 24
- iodine-containing radiopaque organic acid, or mixtures of such acids: 9 to 43

9 Claims, No Drawings

COMPOSITION FOR OCCLUSION OF DUCTS AND CAVITIES OF HUMAN BODY

FIELD OF THE INVENTION

The present invention relates generally to medicine and more specifically to compositions applied for occlusion of ducts and cavities in human organism, e.g., for plugging or filling pancreatic dusts, blood vessels, the bronchi, cysts, abscesses or dental canals.

BACKGROUND OF THE INVENTION

The compositions made use of for occlusion of ducts and cavities of human body must satisfy a number of specific requirements. Such compositions must feature:
1. Biocompatibility
2. Low initial viscosity (under 50 centipoise).
3. Fluidity in the air for at least 10 or 15 minutes and ability to render into solid state within 1 to 3 minutes upon being injected into a duct or cavity.
4. Adhesion to the ductal or cavitary wall.
5. Ability to be destructed and taken out of the organism within one to three months.
6. Radiopacity
7. Antiseptic properties.

Known in the art nowadays are compositions for occlusion of ducts and cavities of human body, based on silicones (cf. a paper by D. F. Blagovidov et al., in the journal 'Klinicheskaya khirurgia', 1982 No. 11, pp. 10–14. These compositions are biocompatible, produce no local irritating effect, retain fluidity in the air for a prolonged period of time, and are radiopaque. However, the aforementioned compositions possess too high viscosity which impedes their injection into ducts or cavities. Besides, the silicone-based compositions are devoid of adhesion to the walls of ducts or cavities, which might result in 'expelling' of the preformed plug out of the ducts and in recanalization thereof, as well as in formation of vacant spaces or passages in between the plug and the ductal walls, which makes the surgical procedure ineffective. Prolonged (over 10 minutes) polymerization time upon getting in contact with body tissues adds to complexity involved in handling the silicone-based occluding compositions, might result in back flowing of such a composition through the accessory pancreatic duct during surgery and hence in incomplete occlusion of the pancreatic ducts. Silicone-based compositions do not possess antiseptic properties, are incapable of developing biodestruction processes, that is, they turn into alien bodies after having performed their function and might prove to be a focus of infection.

Known in the art is another composition for occlusion of ducts and cavities of human body, based on an alcoholic solution of amino-acids, i.e., Prolamine (otherwise called ethibloc). The composition features low initial viscosity, retains fluidity in the air for a prolonged period of time and possesses radiopacity and antiseptic properties (cf. Gebhardt Ch., Stolte M. Lang. Arch. Chir., 1978, Bd. 346, H. 3, S. 149–166). On the other hand, ethibloc features rather long (15 to 20 minutes) setting period upon setting in contact with human tissues which might lead to backward flow of the composition and hence to no effect of the surgical procedure performed. Furthermore, ethibloc is not adhesive to the ductal walls, which might result in "expulsion' of the thus-formed plug, formation of vacant spaces or passages between the plug and the walls of ducts or cavities and hence in recanalization of the ducts and in no effect of the surgery performed. Too rapid (within 11 to 14 days) destruction of the composition and its elimination from the organism results in recanalization of the pancreatic duct system till the complete atrophy is developed, which in particular, results in some cases of occlusion of pancreatic ducts out in incomplete atrophy of the exocrinous tissue of the pancreas. In addition, ethibloc features as short shelf time as three months which lays additional obstacles to its application.

There are also known compositions for occlusion of ducts and cavities of human body based on quick-polymerizing monomers, namely alpha-cyanoacrylates, in particular, esters of alpha-cyanoacrylic acid (cf. Little J. M., Laner C. Surgery, 1977, v. 81, No. 3, pp. 243–249). Said compositions are in fact low-viscosity liquids quickly polymerizable in thin layer upon getting in contact with body tissues, biocompatible and capable of undergoing biodestruction. There is also known application of compositions based on alpha-cyanoacrylates for occlusion of the pancreatic ducts aimed at embolization of blood vessels. It is common knowledge that cyanoacrylates are capable of polymerizing very rapidly (within a few seconds) on getting in contact with body tissues, which might eventuate in incomplete occlusion of ducts or cavities. Fast polymerization of alpha-cyanoacrylates and their being incapable of polymerizing uniformly in a duct or cavity might result in formation of separate conglomerates of the polymer lengthwise the duct, thus rendering the performed surgery ineffective. In addition, use of cyanoacrylates might lead to sticking of the catheter through which the composition has been injected, to the ductal wall. The fact that cyanoacrylates are devoid of antiseptic properties and radiopacity adds to difficulties in handling such compositions.

Thus, none of the compositions of the character set forth hereinabove and now in current use meets all requirements imposed on materials for occlusion of ducts and cavities of human body.

SUMMARY OF THE INVENTION

It is a primary and essential object of the invention to provide such a composition for occlusion of ducts and cavities of human body that would be biocompatible and radiopaque, feature low initial viscosity, prolonged (at least 10 minutes) polymerization time when exposed to the open air, optimum (1 to 3 minutes) polymerization period when in body ducts or cavities, biological destruction period of one to three months, and possess antiseptic properties, as well as adequate adhesion to the ductal and cavitary walls.

With the foregoing and other objects the invention resides in the fact that there is proposed such a composition for occlusion of ducts and cavities of human body that comprises alpha-cyanoacrylates and wherein, according to the invention, there are also contained dimethylsulphoxide, dimethylketone and an iodine-containing radiopaque organic acid, or mixtures of such acids, the weight percentage ratio of the original constituents being as follows:

alpha-cyanoacrylate 25 to 42
dimethylsulphoxide 12 to 25
dimethylketone 20 to 24
iodine-containing radiopaque organic acid or mixtures of such acids: 9 to 43

To prolong the period within which the plug retains its solidity, the composition for occlusion of ducts and cavities of human body may additionally be doped with polyvinylacetate having a molecular mass of 15000 to 25000, in an amount of 5 to 11 weight percent of the total amount of alpha-cyanoacrylate.

Use of the components enlisted above in the aforementioned ratio provides for a whole set of the physicochemical and medicobiological characteristics required for the present composition.

The proposed composition may comprise as alpha-cyanoacrylates such ones as, e.g., ethyl-alpha-cyanoacrylate, ethoxyethyl-alpha-cyanoacrylate, or a mixture thereof.

The composition for occlusion of ducts and cavities of human body may comprise as the iodine-containing radiopaque organic acids such ones as alpha-phenyl-beta-(3,5-diiodo-4-hydroxyphenyl) propionic acid 3-acetylaminomethyl-5-acetylamino-2,4,6-3-iodobenzoic acid, or alpha-(3-amino-2,4,6-3-iodobenzyl) butyric acid.

With the percentage content of alpha-cyanoacrylate less than 25 the composition does not possess adhesive properties, while its biological destruction occurs within 15 and 25 days. When the alpha-cyanoacrylate percentage content exceeds 42 the composition solidifies very quickly on getting in contact with body tissues the setting time being under one minute).

The weight percentage content of dimethylsulphoxide between 12 results in a longer setting time (up to 4 or 6 minutes) of the composition on its getting contact with body tissues, which might eventuate in a back flow of the composition. With the dimethylsulphoxide percentage content above 25 the period of polymerization of the composition in the air is badly reduced (below ten minutes), which complicates much the handling of the composition. With the weight percentage content of iodine-containing radiopaque organic acids below 9 radiopacity of the resultant plug is not provided. The weight percentage content of said acids exceeding 44 results in a slower rate of solidification of the composition on getting in contact with human tissues and in a rather quick loss of solidity by the resultant plug. Application of dimethylketone in the aforespecified quantity in combination with other components of the composition provides for the necessary polymerization time of the composition in the air on getting in contact with body tissues.

The herein-proposed composition for occlusion of ducts and cavities of human body has been tested experimentally on aminals and in humans clinically. The composition has been tested for efficacy in occlusion of the pancreatic ducts on intact pancreatic glands of sexually mature mongrel dogs weighing from 6 to 35 kg. The procedure is as follows. The supramedian laparotomy is carried out under intravenous hexenal anesthesia; the minor (accessory) pancreatic duct is ligated; a polyvinylchloride catheter is introduced extraduodenally into the major pancreatic duct for a depth of 0.3 to 0.5 cm and fixed by ligation therein. The proposed composition is injected within 30 to 50 seconds along the catheter in an amount of 0.6 to 2 ml, whereupon the catheter is withdrawn and the duct is ligated. As the control the occlusion of the pancreatic ducts has been performed according to the same prodedure, using a silicone elastomer and ethylalpha-cyanoacrylate. The surgical procedure is followed by determining the changes in the level of amylase, trypsin, immunoreactive insulin, C-peptide, glucose. Some macroscopic and histologic examinations are carried out in different postoperative terms to study into the rate of atrophy of the pancreas, the decomposition rate of the thus-formed polymer, the rate of positive results.

The rate of positive results of studies performed is expressed by the following relationship and is determined from the formula $n = (A)/A_1 \cdot 100\%$, where n means the rate of positive results, A is the number of animals that have developed complete atrophy of the pancreas, A, stands for a total amount of test animals The rate of atropy is determined by the formula: $V = (1)/t$, where V is the rate of atrophy and t is the lapse of time, within which complete atrophy of the exocrinous portion of the pancreas takes place, characterized by the absence of acinar cells upon histologic examination.

The rate of the polymer decomposition is in fact the lapse of time within which the preformed polymer plug is completely destructed and brought out of the organism. The rate of decomposition is determined macroscopically against the absence of polymer in the major pancreatic duct upon postmortem examination of the test animals.

The results obtained are tabulated in Tables 1 and 2.

TABLE 1

Effect of the proposed composition on variations in the amylase level

| Chemical substance applied | Number of test dogs | Maximum elevation of amylase level (percent of the initial amylase level) | Duration of hyperamylasemia (days) |
|---|---|---|---|
| 1 | 2 | 3 | 4 |
| Proposed composition | 25 | 550 | 10 ± 2 |
| Silicone elastomer | 15 | $2120^x$ | $15 \pm 3^x$ |
| Ethyl-alpha-cyanoacrylate | 10 | 715 | 14 ± 2 |
| $^x$Statistically valid difference | $p\ 0.05$ | | |

TABLE 2

Effect of the proposed composition on the rate of pancreas atrophy and percentage of positive results

| Chemical substance applied | Number of test dogs | Rate of pancreas atrophy (days) | Percentage of positive results |
|---|---|---|---|
| Proposed composition | 25 | 45 ± 7 | 100 |
| Silicone elastomer | 15 | $76 \pm 14^x$ | $70^x$ |
| Ethyl-alpha-cyanoacrylate | 10 | $65 \pm 11^x$ | $60^x$ |
| $^x$Statistically valid difference | $p\ 0.05$ | | |

No statistically reliable difference between the aforestated compositions has been found upon studying the changes in the level of trypsin, immunoreactive insulin, C-peptide, glucose.

When investigating into the polymer decomposition rate, the polymer has been found to completely fill the major pancreatic duct as well as the ducts of the 1st and 2nd order in 15 days after surgery. 1 to 1.5 months after surgery the polymer has been observed to lodge in the major pancreatic duct as individual conglomerates. No polymer is detected in the major pancreatic duct on postmortem examination 2 or 3 months after surgery.

In a separate run of experiments the proposed composition has been tested for applicability in endoscopic occlusion. With this purpose in view, laparotomy is immediately followed by duodenotomy. The major pancreatic duct is catheterized transduodenally, whereupon the proposed composition for occlusion of ducts and cavities of human body is injected without ligating the accessory pancreatic duct in an amount equal to the volumetric capacity of the entire system of the pancreatic ducts. As the control a similar surgical procedure has been performed using silicone elastomer as the occluding composition. The complete pancreas atropy has occurred in 6 test dogs out of 7 that have been given the proposed composition for occlusion of the pancreatic ducts (the percentage of the positive results being 86), whereas the complete pancreas atrophy has been found to occur only in two out of six test dogs, wherein occlusion has been genuine with silicone elastomer (the percentage of positive results being 33).

Thus, experimental application of the proposed composition for occlusion of the pancreatic ducts brings about 100-percent atrophy of the exocrinous portion of the pancreas, the function of the Langerhans' islets remaining unaffected, which is much more statistically valid as compared with other compositions. The rate of atrophy of the pancreas exocrinous portion is enhanced, i.e., the time required for the complete atrophy of the acinar tissue is reduced, the fact that is of paramount importance from the viewpoint of clinical application of the proposed composition. In addition, manifestations of acute edematous pancreatits subside significantly after occlusion of the pancreatic ducts with the use of the proposed composition, which is evidenced by a lower elevation of amylase and shorter duration of hyperamylasemia. The proposed composition for occlusion of ducts and cavities of human body is much more efficacious, as compared with silicone elastomer, in experimental endoscopic occlusion of the pancreatic ducts, which manifests itself in higher percentage of the postocclusion positive results.

The proposed composition has been tested for efficacy in experimental embolization of blood vessels. Experiments have been conducted on ten male rabbits weighing 3 to 3.5 kg each, under general ether anesthesia. The composition taken in an amount of 5 to 10 ml is injected into the femoral artery through a 30 to 50 cm long, 1 mm diameter catheter. The experiments carried out demonstrate that the composition can readily be injected into blood vessels through the catheter of the aforementioned calibre and length, whereby a possibility is provided for the composition to administer into various blood vessels of both medium and small calibre. Test animals tolerate well the surgical procedure for injection of the composition into the femoral artery, no symptoms of a general toxic effect being observed. A clear-cut embolizing effect is attained in 100 percent of the cases.

The proposed composition for occlusion of ducts and cavities of human body has been tested in 17 patients who have been treated in three clinical hospitals. According to the diagnoses the patients fall into the following groups:
Posttraumatic external pancreatic fistula: 4
Chronic pancreatitis 7
Tumor of the pancreatic head 4
Total hemorrhagic pancreatonecrosis: 2
Age span of the patients is 28 and 73 years.

The patients were subjected to a general clinical examination, endoscopic retrograde pancreatocholangiography, sonography of the liver, biliary tract, pancreas both within the pre- and postoperative periods. Roentgenography of the abdominal viscera was also carried out.

One patient (out of the four patients in whome occlusion of the fistular cavity and of part of the pancreatic duct was carried out) developed recanalization of the duct system within the postoperative period that required repeated occlusion. No other postoperative complications were observed. No reliable evidence about any changes in the state of the patients after occlusion of the fistular cavity was obtained by the general clinical examination procedure. Sonographic examinations revealed induration and gradual reduction of the pancreas portion involved in the fistula. Observation X-ray radiography demonstrated that radiopacity of the composition for occlusion of ducts and cavities of human body retained within 10 to 15 days after surgery, which made it possible to carry out occlusion of the fistular cavity and of the pancreatic ducts under radiological monitoring, as well as to perform postoperative control of the location of the composition for occlusion of ducts and cavities of human body. An average period of postoperative in-hospital stay of the patients was 5 to 7 days.

Glucose tolerance tests carried out in six and twelce months after surgery demonstrated normal functioning of the Langerhans' islets.

In seven patients there was carried out occlusion with the aid of the proposed composition for a severe form of chronic painful pancreatitis, of whom five patients were given the procedure within the intraoperative period, and two patients, through the endoscope. The surgery involved laparotomy, duodenotomy, pappillosphincterotomy, catheterization of the major pancreatic duct, and total occlusion of the pancreatic duct system with the aid of the proposed composition for occlusion of ducts and cavities of human body, whereupon a pursestring suture was applied to the opening of the major pancreatic duct and tied up after withdrawal of the catheter. Endoscopic occulsion was carried out after pancreatographic examination in order to confirm correct positioning of the catheter. In all the patients operated upon their was observed moderate hyperamylasemia with the postoperative period, on the average for a period up to four days after surgery. No other postoperative complications were observed. All the patients got rid of pain. Observation X-ray radiography of the abdominal viscera revealed that radiopacity of the proposed composition retained as long as the ten or fifteen days after surgery No cyst formation was detected upon sonography. All the patients operated upon were subsequently subjected to the control investigation of the function of the Langerhans' islets (that is, to the glucose tolerance test), which showed the absence of the diabetes mellitus. The patients in whome endoscopic occlusion was made have been under observation for more than a year, no relapses being noted.

In four patients there was performed occlusion of the pancreatic stump after the pancreatoduodenal resection made for a tumor of the pancreatic head. No complications were observed on the part of the pancreatic stump within the postoperative period, nor dribbling of the pancreatic juice through the drains out of the abdominal cavity. In two patients there was observed during surgery microfocal fat pancreatonecrosis, which was arrested after occlusion of the pancreatic ducts of the pancreatic stump with the aid of the proposed composition for occlusion of ducts and cavities of human body.

In two patients there was performed occlusion of pancreatic ducts for total hemorrhagic pancreatonecrosis. There were carried out laparotomy, chloecystectomy, transduodenal papillosphinoterotomy, and occlusion of the pancreatic ducts.

The general clinical examinations carried out within the postoperative period, and examinations of amylase and trypsin, gave evidence of rapid (within one or two weeks) subsiding of the inflammatory process.

Intoxication phenomena were observed within two or three days.

No complications on the part of the pancreas were noted within the postoperative period, nor there were detected suppuration of the pancreas necrotic foci and flowing of the pancreatic juice through the drains out of the abdominal cavity. The control glucose tolerance tests carried out in six and twelve months after surgery revealed a mild form of the diabetes mellitus in one patient.

Subacute toxicologic experiment revealed no negative effect of the extracts of the proposed composition for occlusion of ducts and cavities of human body on the biological test-subjects (that is, isolated erythrocytes, isolated frog's heart, isolated bull's sexual cells). The studied functions of the test animals' organism exhibited no substantial difference from those of the control animals (that is, the functions of CNS, liver, kidneys, etc.).

Thus, the proposed composition meets all requirements imposed upon compositions for occlusion of ducts and cavities of human body. The proposed composition is biocompatible, features low initial viscosity, retains fluidity in the air for 10 to 15 minutes, is polymerizable in the ducts and cavities within 1 to 3 minutes, possesses good adhesion to the walls of ducts and cavities, is destructable and is brought out of the organism for one to three months, and features good radiopacity and antiseptic properties.

Clinical trials of the proposed composition for occlusion of ducts and cavities of human body, carried out by the applicants, have proven that the composition is convenient in handling and application. Injection of the composition can be monitored against an X-ray screen. Radiopacity of the proposed composition retains within 10 to 15 days after surgery, which makes it possible to keep watch on the location of the composition in the duct system. No postoperative complications are observed. Glucose tolerance tests carried out in every follow-up term (within one year after surgery) give evidence of a normal functioning of the insular apparatus. There are observed, within long-term follow-ups (up to one year), no cases of incomplete occlusion of the pancreatic ducts, recanalization of the duct system, or cyst formation. It is due to low viscosity and optimum polymerization periods of the proposed composition upon getting in contact with body tissues that the composition is readily injectable through an endoscope and gets polymerized immediately after injection. Application of the composition for occlusion of the pancreatic ducts in total hemorrhagic pancreatonecrosis results in subsidence of the inflammatory process, atrophy of the exocrinous portion of the pancreas without formation of abscesses or cysts.

Detailed Description of the Invention

The process for producing the composition for occlusion of ducts and cavities of human body is simple in technological implementation and is carried into effect as follows.

The process flowsheet production of the proposed composition is an follows:

Alpha-cyanoacrylates are taken either individually or in a mixture, next added thereto is dimethylketone in an amount of 5 to 10 weight percent. Thus, the first component of the composition is obtained. Then there is taken an iodine-containing radiopaque organic acid, or a mixture of such acids, and added thereto are dimethylsulphoxide and the rest of dimethylketone, taken in the aforestated ratio. Thus, the second component of the composition is obtained. Both of the aforesaid components may be stored for a prolonged period of time (over one year) in a hermetically sealed package at a temperature of 0±5° C.

To produce the composition for occlusion of ducts and cavities of human body, both of the constituents are to be intermixed immediately before use.

To promote understanding of the invention, the following specific exemplary embodiments are given hereinbelow.

EXAMPLE 1

The composition produced features the following weight percentage ratio of the constituents thereof:
ethyl-alpha-cyanoacrylate: 12.5
ethoxyethyl-alpha-cyanoacrylate: 12.5
dimethylsulphoxide: 15
dimethylketone: 22
alpha-phenyl-beta-(3,5-diiodo-4-hydroxyphenyl)propionic acid: 38

Added to a mixture of 0.125 g ethyl-alpha-cyanoacrylate and 0.125 g ethoxyethyl-alpha-cyanoacrylate is dimethylketone in an amount 0.1 g to obtain the first component of the composition. Then added to 0.38 g alpha-phenyl-beta-(3,5-diidoo-4-hydroxphenyl)propionic acid are 0.15 g dimethylsulphoxide and 0.12 g dimethylketone, the ingredients are thoroughly mixed to obtain the second component of the composition. The thus-obtained components may be kept stored in a hermetically sealed container at 0±5° C. for a prolonged period of time (over one year). Both of the components are to be intermixed carefully immediately before use.

The polymerization time of the thus-obtained composition in the air at 25° C. is 12 minutes. The polymerization rate of the composition on getting in contact with body tissues is 15. minutes. The composition has been tested experimentally on a mongrel dog weighing 8 kg. The supramedian laparotomy was carried out under general hexenal anesthesia. The accessory pancreatic duct was ligated. The major pancreatic duct was catheterized extraduodenally with the aid of a dia. 1 mm catheter, which was fixed in place with a ligature.

The aforesaid composition was injected through the catheter for 45 seconds, whereupon the catheter was withdrawn, and the duct was ligated. The dog was put on a standard diet within the postoperative period. No complications on the part of the pancreas were observed. On postmortem examination in 45 days after surgery there was noted atrophy of the pancreas, and absence of the plug in the major pancreatic duct. On histologic examination there was detected complete atrophy of the acinar tissue, whereas the Langerhans' islets remained unaffected.

EXAMPLE 2

The composition obtained features the following weight percentage ratio of the constituents thereof:
 ethyl-alpha-cyanoacrylate: 21
 ethoxyethyl-alpha-cyanoacrylate: 21
 dimethylsulphoxide: 12
 dimethylketone: 24
 3-acetylaminomethyl-5-acetylamino-2,4,6-3-iodobenzoic acid: 22

The composition is produced according to the process described in Example 1. The polymerization time of the composition in the air at 25° C. is 11 minutes. The rate of polymerization of the composition on getting in contact with body tissues is 1 minutes.

The composition has been trialled clinically in male patient C aged 60, operated upon for total hemorrhagic pancreatonecrosis. The patient was subjected to choledochotomy, papillosphincterotomy, and retrograde occlusion of the pancreatic ducts with the aid of the proposed composition for occlusion of ducts and cavities of human body, taken in an amount of 7 ml. An intensive infusion therapy was carried out within the postoperative period. No complications on the part of the pancreas were observed within the postoperative period. Radiopacity of the composition, which was checked with the aid of observation X-ray radiography of the abdominal viscera, was found to remain up to the 15th after surgery, which made it possible to monitor the location of the composition.

EXAMPLE 3

The composition obtained features the following weight percentage ratio of the constituents thereof:
 ethyl-alpha-cyanoacrylate: 10
 ethoxyethyl-alpha-cyanoacrylate: 12
 polyvinylacetate having a molecular mass of 15000: 8
 dimethylsulphoxide: 25
 dimethylketone: 21
 alpha-(3-amino-2,4,6-3-iodobenzyl butyric acid: 24

The composition is produced by the process described in Example 1. The polymerization time of the composition in the air at 25° C. is 10 minutes, the polymerization rate of the composition on getting in contact with body tissues is 2.5 minutes.

The composition has been trialled clinically in male patient P., aged 46, operated upon for cancer of the pancreatic head. Radical pancreatoduodenectomy according to Whipple was performed, involving occlusion of the pancreatic stump duct system by injecting the composition (3 ml) for occlusion of ducts and cavities of human body. It should be noted that surgery revealed microfocal fat necrosis in the region of the pancreatic tail. Postoperative coursing uneventful. Duration of postoperative hyperamylasemia—5 days. No pancreatic juice discharge through the drains was observed in the postoperative period. The patient was dismissed in satisfactory state in 17 days after surgery.

EXAMPLE 4

The composition obtained features the following weight percentage ratio of the constituents thereof:
 ethyl-alpha-cyanoacrylate: 15
 ethoxyethyl-alpha-cyano-acrylate: 10
 polyvinylacetate having a molecular mass of 25000: 11
 dimethylsulphoxide: 18
 dimethylketone: 20
 3-acetylaminomethyl-5-acetylamino-2,4,6-iodobenzoic acid: 9
 alpha-phenyl-beta-(3,5-diiodo-4-hydroxyphenyl)propionic acid: 17

The composition is obtained according to the process described in Example 1. The polymerization time of the thus-obtained composition when exposed to the air at 25° C. is 14 minutes. The rate of polymerization on getting in contact with body tissues is 15. minutes. The composition has been tested in a chronic experiment on a mongrel dog weighing 20 kg, according to the surgical procedure described in Example 1. Postmortem examination of the sacrificed animal carried out in 15 days after surgery revealed that the polymer plug filled the major pancreatic duct and the first- and second-order ducts in a solid layer. There was moted pronounced atrophy of the acinar pancreatic tissue, as well as proliferation of the fibrous tissue. The Langerhans' islets remained unaffected.

EXAMPLE 5

The composition obtained features the following weight percentage ratio of the constituents thereof:
 ethyl-alpha-cyanoacrylate: 17
 ethoxyethyl-alpha-cyanoacrylate: 17
 dimethylsulphoxide: 19
 dimethylketone: 22
 alpha-phenyl-beta-(3,5-diiodo-4-hydroxyphenyl)propionic acid: 25

The composition is obtained according to the process described in Example 1. The polymerization time of the composition when exposed to the air at 25° C. is 12 minutes, the polymerization time on getting in contact with body tissues is 2 minutes. The composition has been trialled clinically in male patient B aged 38, suffering from a severe form of chronic painful pancreatitis. Once the patient had been subjected to endoscopic retrograde pancreatocholangiography that revealed the catheter staying in the major pancreatic duct, he was given 5 ml of the proposed composition for a period of 50 seconds, with the ratio of its components as described hereinabove. The catheter was withdrawn from the pancreatic ducts just after the injection of the composition. No backward flowing of the composition was observed. The composition was injected under monitoring on an X-ray screen. The postoperative period uneventful. The control X-ray radiography carried out in ten days after surgery detected the polymer located in the major pancreatic duct. The patient was relieved of pain immediately after surgery. The patient has not been complaining of pain within a year after surgery, he is not put on a diet, and has gained 5 kg in weight.

EXAMPLE 6

The composition obtained features the following weight percentage ratio of the constituents thereof:
 ethyl-alpha-cyanoacrylate: 12.5
 ethoxyethyl-alpha-cyanoacrylate: 12.5
 dimethylsulphoxide: 12
 dimethylketone: 20
 3-acetylaminomethyl-5-acetylamino-2,4,6-3-iodobenzoic acid: 43

The composition is obtained according to the process described in Example 1. The polymerization time of the composition when exposed to the air at 25° C. is 10 minutes, the polymerization rate on getting in contact with body tissues is 3 minutes. The composition has been trialled clinically in a male patient, aged 28, suffer-

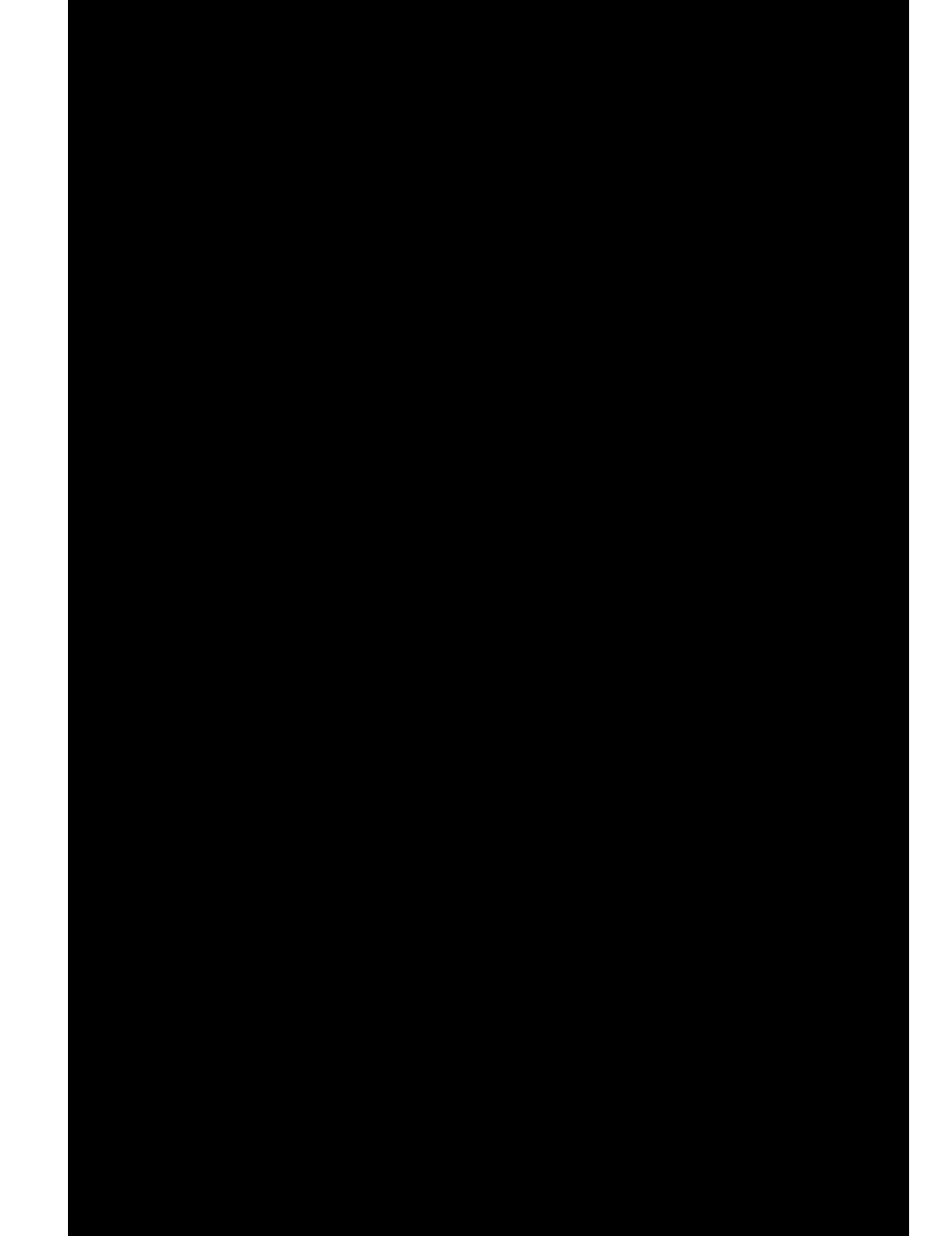

wound was stitched up. Postoperative coursing smooth and uneventful. The dog was sacrificed in 15 days after the occlusion. On postmortem examination the pancreas appeared much indurated, somewhat atrophied. The major pancreatic duct exhibited the fragments of the polymer plug in the form of individual conglomerates. Patency of the pancreatic duct system was restored.

EXAMPLE 11

The composition obtained features the following weight percentage ratio of the constituents thereof:
  ethyl-alpha-cyanoacrylate: 13
  ethoxyethyl-alpha-cyanoacrylate: 13
  dimethylsulphoxide: 8
  dimethylketone: 20
  alpha-phenyl-beta-(3,5-diiodo-4-hydroxyphenyl)propionic acid: 46

The composition is obtained according to the process described in Example 1. The polymerization time of the composition when exposed to the air at 25° C. is 26 minutes. The polymerization time on getting in contact with body tissues is 8 minutes. The composition has not been tested in a chronic experiment as failing to meet the requirements imposed thereon.

EXAMPLE 12

The composition obtained features the following weight percentage ratio of the constituents thereof:
  ethyl-alpha-cyanoacrylate: 26
  ethoxyethyl-alpha-cyanoacrylate: 26
  dimethylsulphoxide: 16
  dimethylketone: 24
  3-acetylaminomethyl-5-acetylamino-2,4,6-3-iodobenzoic acid: 8

The composition is obtained according to the process described in Example 1. The thus-obtained composition is polymerizable when exposed to the air at 25° C. within 14 minutes. The polymerization time of the composition on getting in contact with body tissues is 35 seconds. The composition has been tested in an acute experiment on a dog weighing 14 kg, the surgical procedure being as described in Example 1. An observation X-ray radiographic examination of the abdominal viscera revealed no radiopacity in the pancreas projection. On postmortem examination of the animal in an hour after surgery numerous foci of hemorrhagic necrosis were observed, concerned with too early polymerization of the composition and with the resultant rupture of the interlobular ductules. The composition has not been tested in chronic experiments as not meeting the requirements imposed thereon.

What is claimed is:

1. A composition for occlusion of ducts and cavities of the human body, comprising alpha-cyanoacrylates, dimethylsulfoxide, dimethylketone, an acid selected from the group of iodine-containing radiopaque organic acids and of mixtures thereof, with the weight percentage ratio of the constituents as follows:
   alpha-cyanoacrylate: 25 to 42
   dimethylsulfoxide: 12 to 25
   dimethylketone: 20 to 24
   iodine-containing radiopaque organic acid, or mixture of such acids: 9 to 43.

2. The composition as in claim 1, wherein the iodine-containing radiopaque organic acids in the composition are compounds selected from the group consisting of alpha-phenyl-beta-(3,5-diiodo-4-hydroxyphenyl)propionic acid, 3-acetylaminomethyl-5-acetylamino-2,4,6-3-iodobenzoic acid and alpha-(3-amino-2,5,6-3-iodobenzyl)butyric acid.

3. The composition as in claim 1, further comprising polyvinylacetate having a molecular mass of 15000 to 25000 in a proportion of 5 to 11 weight percent of the amount of alphacyanoacrylate.

4. A composition for occlusion of ducts and cavities of the human body consisting of alpha-cyanoacrylates, dimethylsulfoxide, dimethylketone, an acid selected from the group consisting of iodine-containing radiopaque organic acids and of mixtures thereof, with the weight percentage ratio of the constituents as follows:
   alpha-cyanoacrylate: 25 to 42
   dimethylsulfoxide: 12 to 25
   dimethylketone: 20 to 24
   iodine-containing radiopaque organic acid, or mixtures of such acids: 9 to 43.

5. The composition as in claim 4, wherein the iodine-containing radiopaque organic acids in the composition are compounds selected from the group consisting of alpha-phenyl-beta-(3,5,diiodo-4-hydroxyphenyl)propionic acid, 3-acetylaminomethyl-5-acetylamino-2,4,6-3-iodobenzoic acid and alpha-(3-amino-2,4,6-3-iodobenzyl)butyric acid.

6. The composition as in claim 4, further consisting of polyvinylacetate having a molecular mass of 15000 to 25000 in a proportion of 5 to 11 weight percent of the amount of alpha-cyanoacrylate.

7. A method for occlusion of pancreatic ducts comprising
   (a) preparing a composition comprising alpha-cyanoacrylates, dimethylsulfoxide, dimethylketone, an acid selected from the group of iodine-containing radiopaque organic acids and of mixtures thereof, with the weight percentage ratio of the constituents as follows:
      alpha-cyanoacrylate: 25 to 42
      dimethylsulfoxide: 12 to 25
      dimethylketone: 20 to 24
      iodine-containing radiopaque organic acid, or mixtures of such acids: 9 to 43
   (b) ligating the accessory pancreatic duct of a patient
   (c) catheterizing the patient's major pancreatic duct
   (d) injecting said composition through the catheter
   (e) withdrawing the catheter
   (f) ligating the duct.

8. The method as in claim 7 wherein the iodine-containing radiopaque organic acids in the composition are compounds selected from the group consisting of alpha-phenyl-beta-(3,5-diiodo-4-hydroxyphenyl)propionic acid, 3-acetylaminomethyl-5-acetylamino-2,4,6-3-iodobenzyl)butyric acid.

9. A method for occlusion of pancreatic ducts comprising
   (a) preparing a composition consisting of alpha-cyanoacrylates, dimethylsulfoxide, dimethylketone, an acid selected from the group of iodine-containing radiopaque organic acids and of mixtures thereof, with the weight percentage ratio of the constituents as follows:
      alpha-cyanoacrylate: 25 to 42
      dimethylsulfoxide: 12 to 25
      dimethylketone: 20 to 24
      iodine-containing radiopaque organic acid, or mixtures of such acids: 9 to 43
   (b) ligating the accessory pancreatic duct of a patient
   (c) catheterizing the patient's major pancreatic duct
   (d) injecting said composition through the catheter
   (e) withdrawing the catheter
   (f) ligating the duct.

* * * * *